(12) United States Patent
Henriksen et al.

(10) Patent No.: US 8,101,383 B2
(45) Date of Patent: Jan. 24, 2012

(54) METHOD FOR SYNGAS-PRODUCTION FROM LIQUEFIED BIOMASS

(75) Inventors: Niels Henriksen, Fredericia (DK); Martin Høgh Møller, Fredericia (DK); Jan Larsen, Tommerrup (DK)

(73) Assignee: Dong Energy Power A/S, Fredericia (DK)

( * ) Notice: Subject to any disclaimer, the term of this patent is extended or adjusted under 35 U.S.C. 154(b) by 267 days.

(21) Appl. No.: 12/302,505

(22) PCT Filed: May 24, 2007

(86) PCT No.: PCT/IB2007/051962
§ 371 (c)(1), (2), (4) Date: Jun. 4, 2009

(87) PCT Pub. No.: WO2007/138534
PCT Pub. Date: Dec. 6, 2007

(65) Prior Publication Data
US 2009/0305355 A1   Dec. 10, 2009

(30) Foreign Application Priority Data
May 26, 2006   (DK) .................................. 2008 00723

(51) Int. Cl.
*C12P 19/00*   (2006.01)
(52) U.S. Cl. ......................................... 435/72; 435/166
(58) Field of Classification Search .................. 435/72, 435/166
See application file for complete search history.

(56) References Cited

U.S. PATENT DOCUMENTS
5,424,417 A    6/1995 Torget et al.
2004/0262220 A1   12/2004 Binnig et al.

FOREIGN PATENT DOCUMENTS
DE    102 10 178    6/2003

OTHER PUBLICATIONS

Larsen, J. et al., "Integration of a biorefinery working at a high dry matter content with a power plant. Concepts and feasibilities". Oral presentation at 28th Symposium on Biotechnology for fuels and chemicals; Nashville, Apr. 3-May 30, 2006; power point slides.

Jørgensen, H. et al., "Enzymatic hydrolysis of lignocellulose at very high solids concentrations". Oral presentation at 28th Symposium on Biotechnology for fuels and chemicals; Nashville, Apr. 3-May 30, 2006; power point slide.

Jørgensen, H. et al., "Liquefaction of Lignocellulose at High-Solids Concentration". Biotechnology and Bioengineering, Apr. 1, 2007. 96:862-870.

Kristensen, K. et al., "Investigation of factors limiting hydrolysis at high solids concentration", poster presentation at 28th Symposium on Biotechnology for fuels and chemicals; Nashville, Apr. 3-May 30, 2006.

ECN: van der Drift, A.; Boerrigter, H.; Coda, B.; Cieplik, M.K.; Hemmes, K. Entrained Flow Gasification of Biomass: Ash behaviour, feeding issues, and system analyses, ECN-report-C-04-039, 2004.

Giovannozzi-Sermanni, Giovanni; D'Annibale, Alessandro; Perani, Claudio; Porri, Antonio Stazi Silvia Rita; Falesiedi, Giuseppe. Solid-state bioreactors for the sustainability, http://www.unitus.it/dipartimenti/dabac/progetti/ssbioreactors/solidstatebioreactor.htm, 2002.

Hamelinck, C.N.; Faaij, André P.C.; Uil, Herman den; Boerrigter, Harold. Production of FT transportation fuels for biomass; technical options, process analysis and optimization, and development potential, ISBN 90-393-3342-4, Mar. 2003.

Henrich, E.; Dinjus, E. Tar-free, high pressure synthesis gas from biomass, Expert Meeting on Pyrolysis and Gasification of Biomass; Strassbourg, France, Sep. 30-Oct. 1, 2002.

LLC:Frontline BioEnergy, LLC. What is biomass? http://www.frontlinebioenergy.com/id15.html, May 16, 2006.

RRI:Research Reports International. Gasification for Power Generation, 1st Edition, Sep. 2005.

*Primary Examiner* — Herbert J Lilling
(74) *Attorney, Agent, or Firm* — Stites & Harbison PLLC; Marvin Petry (57) ABSTRACT

The present invention relates to methods for syngas-production from biomass enabling the conversion of pre-treated biomasses having a high dry-matter content into electricity or oil-based products such as petrol, diesel, chemicals and plastics through the formation of syngas. The biomasses are converted into a biomass slurry having a suitable particle size and dry-matter content for optimal feeding and gasification in a pressurised gasifier.

27 Claims, 4 Drawing Sheets

Fig. 2: Longitudinal view (left) and transverse view (right) of the 5-chamber hydrolysis reactor

Figure 3

Fig. 3: Concentration of glucose during liquefaction and hydrolysis of pretreated wheat straw at a dry matter content of 20 % (●), 25 % (▼), 30 % (■), 35 % (♦) and 40 % (▲) using an enzyme loading of 7 FPU (g DM)$^{-1}$

Figure 4:

METHOD FOR SYNGAS-PRODUCTION FROM LIQUEFIED BIOMASS

FIELD OF THE INVENTION

The present invention relates to methods for syngas-production from biomass. A method according to the present invention will typically comprise the steps of thermal pre-treatment including removal of alkali compounds followed by an enzymatic treatment of the biomass at a high dry matter content yielding small particles which are subsequently transferred by high-pressure pumping into a pressurised gasifier for subsequent syngas-production. Thus a method according to the present invention enables the conversion of pre-treated biomasses having a high dry-matter content, such as wood, straw and plant deposits into products that substitutes oil-based products such as petrol, diesel, chemicals and plastics through the formation of syngas by use of a gasifier. The pre-treatment of a method according to the present invention typically consist of thermal heating of the biomass to 170-220° C. using pressurised high-temperature steam and/or microwaves, optionally combined with the addition of acid, base or oxidants. The enzymatic treatment of a method according to the present invention enables the conversion of cellulose into polymers and oligomers resulting in a liquefaction of the biomass. A method according to the present invention may include steps for the removal of alkali salts such as chloride, sodium and potassium from the biomass that subsequently can be sold as feed nutrient for use in agriculture. The biomass slurry resulting from pre-treatment and enzymatic treatment of a method according to the present invention will typically consists of particles less than 1 mm making them suitable for optimal utilisation in a gasifier with a short residence time of only a few seconds without producing unwanted tars. The resulting gas can subsequently be used for production of power, fuels, chemicals and heat.

BACKGROUND OF THE INVENTION

A desire to minimise the dependence on coal, oil and gas and to reduce the $CO_2$ emission has intensified the research in areas concerned with the exploitation of renewable biomasses such as wood, straw and plant deposits into oil-based products such as petrol, diesel, chemicals and plastics through the formation of syngas.

Numerous industrial and agricultural processes e.g. municipality operations, food and feed processing and forestry generate biomasses, waste and by-products containing polymeric sugars e.g. in the form of starch, cellulose and hemicellulose. Agribusiness and chemical industries as well as public organisations have considerable interest in developing processes for converting such biomasses into materials of a higher value. However, the majority of processes known today have not yet reached large-scale commercial practice due to their high production cost and high energy demand and thus inherent uncertain economic feasibility.

Besides being important as food and feed, carbohydrates from biomass through syn-gas production can be used as feedstock for a number of industrial processes producing products valuable in the production of oil-based products such as petrol, diesel, chemicals and plastics.

It is therefore evident that if low-cost and abundant resources of carbohydrates can be processed into e.g. syngas at a relatively low energy consumption and thereby can be made available for industrial processing it may have a substantial economic potential.

Biomasses such as wood, straw and plant deposits can be converted into oil-based products such as petrol, diesel, chemicals and plastics through the formation of syngas by use of a gasifier. Syngas consists of CO, $CO_2$, $H_2$, $N_2$, $CH_4$, $H_2O$ and impurities such as $H_2S$ and tars. Gasification is a well-known technology where hydrocarbon bonds are broken down to produce syngas, under the addition of oxygen and steam, preferably under high pressures and temperatures. A gasifier differs from a combustor in that the amount of air or oxygen available inside the gasifier is carefully controlled so that only a relatively small portion of the fuel burns completely. The oxygen level controls that the hydrocarbons do not combust into $CO_2$, but only oxidises partially.

A major obstacle to obtain full benefit from gasification of biomass compared to coal is how to pre-treat the biomass in a way, that makes it suitable to be economically gasified (ECN, 2004). Syngas production from coal gasification has been a commercial available technology for more than 50 years. Coal is relatively easy to grind and feed into a pressurised gasifier, biomass in general however is often very troublesome to grind and fed into a pressurised gasifier. This is due to the fact that most biomass is very inhomogeneous compared to coal, and hence it is difficult to grind it down to a relative homogeneous particle size required for entrained flow gasification where the residence time is very short—in the order of few seconds. Furthermore it is very troublesome to pressurise a solid material, with a very uneven and rather large particle size.

Traditionally, pretreatment of biomasses to be fed into a gasifier have been performed using methods such as direct pulverisation, combustion and pulverisation, production of charred sludge through flash-pyrolysis or production of gaseous fuels through low-temperature fluid-bed gasification which are all combined with different disadvantages concerning energy costs and/or economic costs.

The present invention relates to a method to liquefy the biomass in a way that it becomes a "homogenised liquid" with a rather small particle size and still have a rather high dry matter content (above 20%). The homogenised liquid can economically be pressurised using commercial pumps, and as a consequence it will be possible to feed a pressurised entrained flow gasifier with biomass as bagasse, straw etc.

Depending on the type of biomass intended to be used, several different "pre-treatment" options exist in order to liquefy the biomass.

Pre-treatment is required if a subsequent hydrolysis (e.g. enzymatic hydrolysis) of the polysaccharides requires the break down of an otherwise protecting structure (e.g. lignin) of the plant materials. Several pre-treatment techniques are known. For cereals and grains, this pre-treatment may be in the form of a simple dry milling in order to render the surfaces accessible, but for lignocellulosic biomasses thermal and/or chemical processes are needed as well. A polysaccharide containing biomass consisting of e.g. refined starch does not require said pre-treatment methods prior to enzymatic processing. Pretreatment-processes may be based on acidic hydrolysis, steam explosion, oxidation, extraction with alkali or ethanol etc. A common feature of the pre-treatment techniques is that combined with the action of possible added reactants they take advantage of the softening and loosening of plant materials that occurs at temperatures above 100° C.

Apart from starch the three major constituents in plant biomass are cellulose, hemicellulose and lignin, which are commonly referred to by the generic term lignocellulose. Polysaccharide containing biomasses as a generic term include both starch and lignocellulosic biomasses.

Cellulose, hemicellulose and lignin are present in varying amounts in different plants and in the different parts of the plant and they are intimately associated to form the structural framework of the plant.

Cellulose is a homopolysaccharide composed entirely of D-glucose linked together by β-1,4-glucosidic bonds and with a degree of polymerisation up to 10,000. The linear structure of cellulose enables the formation of both intra- and intermolecular hydrogen bonds, which results in the aggregation of cellulose chains into micro fibrils. Regions within the micro fibrils with high order are termed crystalline and less ordered regions are termed amorphous. The micro fibrils assemble into fibrils, which then form the cellulose fibres. The partly crystalline structure of cellulose along with the microfibrillar arrangement, gives cellulose high tensile strength, it makes cellulose insoluble in most solvents, and it is partly responsible for the resistance of cellulose against microbial degradation, i.e. enzymatic hydrolysis.

Hemicellulose is a complex heterogeneous polysaccharide composed of a number of monomer residues: D-glucose, D-galactose, D-mannose, D-xylose, L-arabinose, D-glucuronic acid and 4-O-methyl-D-glucuronic acid, Hemicellulose has a degree of polymerisation below 200, has side chains and may be acetylated. In softwood like fir, pine and spruce, galactoglucomannan and arabino-4-O-methyl-glucuronoxylan are the major hemicellulose fractions. In hardwood like birch, poplar, aspen or oak, 4-O-acetyl-4-methyl-glucuronoxylan and glucomannan are the main constituents of hemicellulose. Grasses like rice, wheat, oat and switch grass have hemicellulose composed of mainly glucuronoarabinoxylan.

Lignin is a complex network formed by polymerisation of phenyl propane units and it constitutes the most abundant non-polysaccharide fraction in lignocellulose. The three monomers in lignin are p-coumaryl alcohol, coniferyl alcohol and sinapyl alcohol, and they are most frequently joined through arylglyceryl-β-aryl ether bonds. Lignin is linked to hemicellulose and embeds the carbohydrates thereby offering protection against microbial and chemical degradation.

Starch is the most widespread storage carbohydrate in plants and occurs in the form of granules, which differ markedly in size and physical characteristics from species to species. Starch granules are generally quite resistant to penetration by both water and hydrolytic enzymes due to the formation of hydrogen bonds within the same molecule and with other neighbouring molecules. However, these inter- and intra-hydrogen bonds can become weak as the temperature of the suspension is raised. When an aqueous suspension of starch is heated, the hydrogen bonds weaken, water is absorbed, and the starch granules swell. This process is commonly called gelatinization because the solution formed has a gelatinous, highly viscous consistency. Chemically, starch is a natural polymer of glucose, which is generally insoluble but dispersible in water at room temperature and made up of a repeating unit similar to that of cellulose and linked together by α-1,4 and α-1,6glucosidic bonds, as opposed to the β-1, 4glucosidic bonds for cellulose. The units form either a linear chain component, called amylose, or a branched chain component, called amylopectin. Most plant seeds, grains and tubers contain about 20-25% amylose. But some, like e.g. pea starch have 60% amylose and certain species of corn have 80% amylose. Waxy varieties of grains, such as rice, are low in amylose.

Following the pre-treatment, the next step in utilisation of polysaccharide containing biomasses for production of syngas is hydrolysis of the liberated starch, cellulose and hemicellulose into polymeres and oligomeres.

This can be obtained with different enzymes with different modes of action. The enzymes can be added externally or microorganisms growing on the biomass may provide them.

Cellulose is hydrolysed into glucose by the carbohydrolytic cellulases. The prevalent understanding of the cellulolytic system divides the cellulases into three classes; exo-1,4-β-D-glucanases or cellobiohydrolases (CBH) (EC 3.2.1.91), which cleave off cellobiose units from the ends of cellulose chains; endo-1,4-β-D-glucanases (EG) (EC 3.2.1.4), which hydrolyse internal β-1,4-glucosidic bonds randomly in the cellulose chain; 1,4-β-D-glucosidase (EC 3.2.1.21), which hydrolyses cellobiose to glucose and also cleaves of glucose units from celloligosaccharides.

The different sugars in hemicellulose are liberated by the hemicellulases. The hemicellulytic system is more complex than the cellulolytic system due to the heterologous nature of hemicellulose. The system involves among others endo-1,4-β-D-xylanases (EC 3.2.1.8), which hydrolyse internal bonds in the xylan chain; 1,4-β-D-xylosidases (EC 3.2.1.37), which attack xylooligosaccharides from the non-reducing end and liberate xylose; endo-1,4-β-D-mannanases (EC 3.2.1.78), which cleave internal bonds; 1,4-β-D-mannosidases (EC 3.2.1.125), which cleave mannooligosaccharides to mannose. The side groups are removed by a number of enzymes; α-D-galactosidases (EC 3.2.1.22), α-L-arabinofuranosidases (EC 3.2.1.55), α-D-glucuronidases (EC 3.2.1.139), cinnamoyl esterases (EC 3.1.1.-), acetyl xylan esterases (EC 3.1.1.6) and feruloyl esterases (EC 3.1.1.73).

The most important enzymes for use in starch hydrolysis are alpha-amylases (1,4-α-D-glucan glucanohydrolases, (EC 3.2.1.1). These are endo-acting hydrolases which cleave 1,4-α-D-glucosidic bonds and can bypass but cannot hydrolyse 1,6-alpha-D-glucosidic branchpoints. However, also exo-acting glycoamylases such as beta-amylase (EC 3.2.1.2) and pullulanase (EC 3.2.1.41) can be used for starch hydrolysis. The result of starch hydrolysis is primarily glucose, maltose, maltotriose, α-dextrin and varying amounts of oligosaccharides.

Enzymatic liquefaction and hydrolysis of biomass has previously been described. However, in case of pre-treated lignocellulosic biomasses only material consisting of fibres and particles with an average size below 1 inch (25.4 mm) and furthermore having a relatively low dry matter content, i.e. below 20% (w/w), have successfully been liquefied by such a method.

US2004/0262220 describes a method for anaerobic digestion of biomasses with the purpose of producing biogas. The method is unsuitable for the production of syngas as it is anaerobic and is furthermore designed to produce biogas, which in contrast to syngas consists mainly of $CH_4$ and $CO_2$. The pre-treatment of the biomass comprises thermal pre-heating and hydrolysis, however, in contrast to the present invention, thermal pre-heating of the biomass does not surpass 100° C. and hydrolysis results predominantly in mono saccharides which are suitable for fermentation.

U.S. Pat. No. 5,424,417 relates to a method of prehydrolysis of lignocellulose with the purpose of obtaining biomass suitable for further fermentation. The method is based on thermal treatment of 120-240° C. combined with the addition of alkali or acid in a flow-through system and includes a step removing solids. Such a flow-through system is not beneficial for the pre-treatment of biomass for syngas production as the entire slurry is to be pumped into a gasifier.

U.S. Pat. No. 4,645,541 concerns a multi-step method of producing microcrystalline cellulose and glucose from lignocellulosic material. The method comprises thermal pre-treatment of 185-240° C., explosively expelling of the material, extraction of lignin using an organic solvent, filtering and separating the material into cellulose and hemicellulose fractions. Since the purpose of this treatment is to separate lignin from cellulose and hemicellulose, the pre-treatment is much more laborious and energy consuming than what is needed for syngas production and results in particles of 1-10 microns already after the explosive step.

U.S. Pat. No. 4,916,242 concerns a process for thermally and chemically treating lignocellulose-containing biomass with the purpose of producing furfural. The method comprises heating the biomass in a cooking liquor containing pentoses. The liquor is distilled in a separate production plant producing the furfural, and the thermally treated biomass is discharged and hence not used for further production of e.g. syngas.

Gasification is a well-known technology where carbon-containing material is fed into a vessel in the addition of oxygen and steam. Traditionally, pulverised coal has been preferred as hydrocarbon feedstock. A reaction developing excessive heat takes place, the carbon bonds are broken and syngas is produced. Depending on the further use of the syngas, it may need to be cleaned from particles such as sulphur, alkali and mercury. If the syngas is to be burned in a gas turbine the cleaning of the gas is less important than if it is to be used for production synthetic product such as FT diesel, Petrol or methanol. Gasification can be more flexible, efficient and environmentally friendly compared to direct combustion. Gasifiers are also used in Integrated Gasification Combined Cycle (IGCC) power plants allowing a higher efficiency in electricity production in contrast to ordinary coal boilers and steam boilers.

Typically, coal, crude oil, high sulphur fuel oil, petroleum and other refinery residuals has been the preferred raw material for gasification. In a modern gasifier coal is subjected to hot steam and carefully controlled amounts of air or oxygen, under high temperatures and pressures. These conditions cause the carbon molecules in coal to break apart, starting chemical reactions that produce a mixture of hydrogen, carbon monoxide and other gaseous compounds (RRI, 2005). The most important period for coal gasification was during the 1980s and 1990s. Driven by environmental concerns over the burning of coal, gasification became known as a clean way to generate electric power. The first coal gasification electric power plants are now operating commercially (RRI, 2005).

However, substitution of the dwindling fossil fuels by renewable energy and carbon resources such as lignocellulosic biomass sources will be advantageous in the future. Herbaceous by-products from agriculture, mainly cereal straw and strawlike residues are cheap renewables. Wood is a relatively clean fuel and traditional technologies for wood combustion and gasification are well developed whereas the use of herbaceous biomass are more complex and not well developed (Henrich and Dinjus, 2002). Biomass differs from coal in many respects. The most relevant differences refer to ash behaviour, feeding and pressurising properties.

Biomass is generally very variable in respect of structure, content of water, content of alkali and particle size. This complicates the processing of biomass, especially if it is to be treated under pressurised conditions. Therefore, one of the greatest challenges to optimal benefit from gasification is to pre-treat the biomass in a way which makes it suitable to be fed into the gasifier. In comparison with other potential biomasses for syngas production, enzymatically liquefied lignocellulosic biomass obtained by the present method has the great advantage that it is already partially processed and exist in a pumpable, liquid form with suspended particles of limited size (typical below 1 mm).

The calorific value of the biomass is very dependent on the water content, which is therefore a limiting factor for the quality of the syngas developed. A higher combustion temperature results in a syngas containing a lower amount of tar products and methane. On the other hand, a high water content represses the soot development and is thermodynamically favourable in respect to limit $CH_4$ slip exit the gasifier Biomasses such as straw have a high content of alkali such as potassium and sodium.

During the gasification some of this is released in the gas phase and will subsequently condense during the cooling of the gas and result in problems related to fouling and corrosion. In oxygen based entrained flow gasifiers a temperature of 2500° C. can be reached in the combustion zone whereby the majority of the minerals in the biomass will fuse into slag and will therefore not be available for re-delivery into the environment.

There are several gasification methods available, however, gasification using pure oxygen at high temperature and high pressure results in the highest efficiency and best quality syngas (Hamelinck et al., 2003). The central component is the gasifier regulating the oxygen flow such that the hydrocarbons do not combust completely into $CO_2$ but only oxidises partially.

Gasification processes can be divided into four major classes that involve operating pressures up to around 400 bar:
Moving bed/Moving fixed bed
Fluidised bed
Entrained flow
Supercritical Gasification Moving bed gasifiers have a considerable distribution but are mainly suited for solid fuels. The gasifier consists of introducing coarse solids at the top of the gasifier while the oxidant gas and steam are introduced at the bottom of the gasifier. The thermal efficiency of the gasifier is high but since the gasifier produces tars and oils, the gas clean up is complex. Biomass such as straw and liquefied biomass is not suitable for this kind of gasifier.

Fluidised bed gasifiers burn the hydrocarbon feedstock in a bed of heated particles suspended in flowing air. At sufficiently high air velocity, the bed acts as a fluid resulting in rapid mixing of the particles. The fluidising action promotes complete combustion at relatively low temperatures (760-1040° C.) and provides a means to transfer combustion heat efficiently from the bed to steam tubes. The use of sulphur-absorbent chemicals such as limestone or dolomite is indispensable. However, since the absorbents may react with the alkali compounds of the biomass to form a low melting suspension with the risk of plugging the gasifier, removal of alkali from the biomass prior to feeding into the gasifier will supposedly be advantageous. Due to the low temperatures, the residues from fluidised bed gasifiers are less inert than ashes produced in a moving bed gasifier and may require more attention to their disposal in an environmentally secure repository.

Entrained flow gasifiers are the most wide spread gasifiers for commercial purposes. Such gasifiers are usually fed with a coal and water slurry but can also operate on dry coal by use of pneumatics and/or lock hoppers. The biggest advantage of using an entrained flow reactor is the high exit temperatures resulting in a syngas with a very low content of tar and methane. The entrained flow gasifiers is also characterised by having a rather short retention time of say 1-2 seconds. The advantages of such a short retention time, is that very high amounts of coals/biomass can be converted at a relatively small gasifier volume, which is the driving force for choosing entrained flow gasifiers for large scale commercial applications. The disadvantages is on the other hand that the coal/biomass, has to be grinded into very small particles in order to complete the chemical reactions, before it leaves the gasifier. The entrained flow gasifier is very suitable for the production of hydrogen and syngas products. Combustion in this kind of gasifier may result in slagging residuals depending on the potential ash content of the biomass. In a slagging gasifier, the ash forming components melt in the gasifier, flow down the walls of the reactor and finally leave the reactor as a liquid slag (ECN, 2004).

Coal based conventional and well-tested systems require a previous pulverisation of the coal resulting in particles of 40-100 µm. Similar mechanical pre-treatment of biomass such as wood uses up to 0.08 kW electricity/kW wood corresponding to approximately 20% primary energy (ECN, 2004), which is an unacceptable high value.

Different pre-treatments of biomasses to be converted in an entrained flow gasifier has been tested including direct wood pulverisation production of brittle solid by torrefaction and subsequent pulverisation, production of oil/char-slurry by flash pyrolysis and production of gaseous fuel by low temperature fluidised bed gasification (ECN, 2004). In general, coal-fired entrained flow gasifiers are operated on coal powders with a size of typically 50-100 µm. This ensures complete conversion. Since biomass is much more reactive than coal, it is expected that size demands for biomass are less stringent. The ECN (2004) report states, that biomass particles can be as large as 1 mm as far as complete conversion is concerned.

Fast or flash pyrolysis is a relatively simple method that converts about half of lignocellulosic biomass or even more into a pyrolysis liquids. The brittle pyrolysis char is pulverised and suspended in oil to produce pumpable slurry (Henrich and Dinjus, 2002). However, fast pyrolysis requires that the biomass is dried and chopped and further reduced in size using a hammer mill to ensure a fast heatup during pyrolysis. Most reactors suitable for fast pyrolysis use a solid heat carrier such as sand. The fluidisation is obtained by mechanical means. The biofuel particles are mixed with and excess of hot sand above 500° C. and transported in co-current flow with low axial and good radial mixing (Henrich and Dinjus, 2002).

Pre-treatment of biomass at low-temperature pyrolysis or out-burning implies that salts, which may course problems in the gasifier, remain in the material. Alternatively, the salts, which are often useful fertilisers, are bound in residuals and thereby the possibility to re-circulate them into the environment is lost. Furthermore, pre-treatment based on pyrolysis is not a very attractive method, as the efficiency is low.

Feeding of biomass into an entrained gasifier may be done using lock hoppers or piston feeders. In the lock hopper system, the lock hopper is filled with biomass at atmospheric pressure, pressurised to 4000 psi using an inert gas and the solids are fed to the reactor with the help of a rotary feeder (LLC, 2006), screw feeder or by pneumatic transport.

Piston feeding is an alternative for the lock hopper system and has the advantage of little volume and low inert gas consumption. This method has been tested for torrified wood chips (ECN, 2004). This piston feeder consisted of an atmospheric supply bunker, a piston feeder and a pressurised tank Subsequently the biomass can be fed by screw into the gasifier. The experiment showed that if a piston feeder replaced the lock hopper, the inert gas consumption was reduced and the energy penalty was lower than 3% for 1 mm solids.

However, for liquefied biomasses, pressurising systems can be replaced by slurry pumps that are state-of-the-art. The liquid fuel subsequently is atomised and fed to the burner similarly to solid fuel powder (ECN, 2004).

Supercritical Gasification is a process where the feedstock is heated and pressurised to a value higher than the critical point of water (221 bar and 375° C.). When the feedstock is sufficiently heated and pressurised the organic part decomposes into a mixture of hydrogen, methane, carbon monoxide and carbon dioxide. If the amount of water is relatively high compared to the amount of organic materials, all the CO will be converted into hydrogen and carbon dioxide due to the watergas shift reaction. Presently supercritical gasification is under development by i.e. Forschungszentrum Karlsruhe (DE10210178). Due to the fact that the biomass needs to be pressurised up to around 300 bar, the biomass needs to be pumpable. So far this has been solved by fine chopping the biomass and diluting it with water, resulting in a biomass water slurry with a dry matter content of only around 10% based on weight. It will from an efficiency and economically point of view, be a huge advantage to increase the dry matter content to around 20-30%, which is possible with the present invention.

SUMMARY OF THE INVENTION

The present invention concerns a method for syngas-production from biomass. The method comprises a process for the liquefaction of biomasses containing polysaccharides, having a high dry matter content and preferably possessing fibres and particles with large average sizes and to the further utilisation of such processed biomasses for subsequent gasification into syngas which is suitable for processing into petrol, plastics and chemicals or can be used in gas turbine for electricity production.

The present invention relates to a process for liquefaction of and subsequent syngas production from polysaccharide containing biomasses, having a relatively high dry matter content, preferably above 20%. Furthermore, the process is particularly suited for the liquefaction of and subsequent syngas production from polysaccharide containing biomasses consisting primarily of starch, refined starch, cellulose, hemicellulose and lignin, e.g. grains or wheat straw. In the case of lignocellulosic biomasses these are preferably pre-treated by subjection to temperatures between 110-250° C. for 1-60 min in a manner, which secures accessibility of the enzymes to the cellulose. In the thermal pre-treatment pressurised steam and optionally microwaves are used. Washing of the pre-treated biomass can be done simultaneously or afterwards, whereby nutritive salts and smaller sugars such as C5 sugars are washed out. These nutrients may be collected and are suitable for use as additives in feeding stuff, hereby being re-circulated to nature. The pre-treatment may be performed without concern of development of products that inhibit e.g. fermentation and it is thus possible to add chemicals to increase the speed of lignin decomposition, without having to consider whether these (or by-products resulting from there addition) would negatively influence e.g. a subsequent fermentation step. The present invention combines enzymatic hydrolysis based on the combination of carbohydrolytic enzymes with a type of mixing relying on the principle of gravity ensuring the application of mechanical forces, primarily shear and tear forces, to the biomasses. Preferred types of mixing are e.g. free fall mixers such as drum mixers, tumble mixers or similar mixing devices.

The liquefied biomass has a dry-matter content of 20-50% and is pumped into a pressurised gasifier such as an entrained flow gasifier or a gasifier suitable for supercritical gasification. If the calorific value of the liquefied biomass is too low in order to obtain a high outlet temperature exit the gasifier, it might be necessary to add some "extra" hydrocarbons to the gasifier. Such hydrocarbons could be recirculated by-products from the petrol or diesel production, or other low value hydrocarbon products.

In general a high dry matter content of the slurry is preferred. A high dry matter content might increase the viscosity and reduce the pumpability. Adjustment of the viscosity can be made by addition of oil to the liquefied biomass, in combination with adjustment of the heating value. Another way to obtain the same effect is to combine drying with a prolonged liquefaction.

Figure 1:
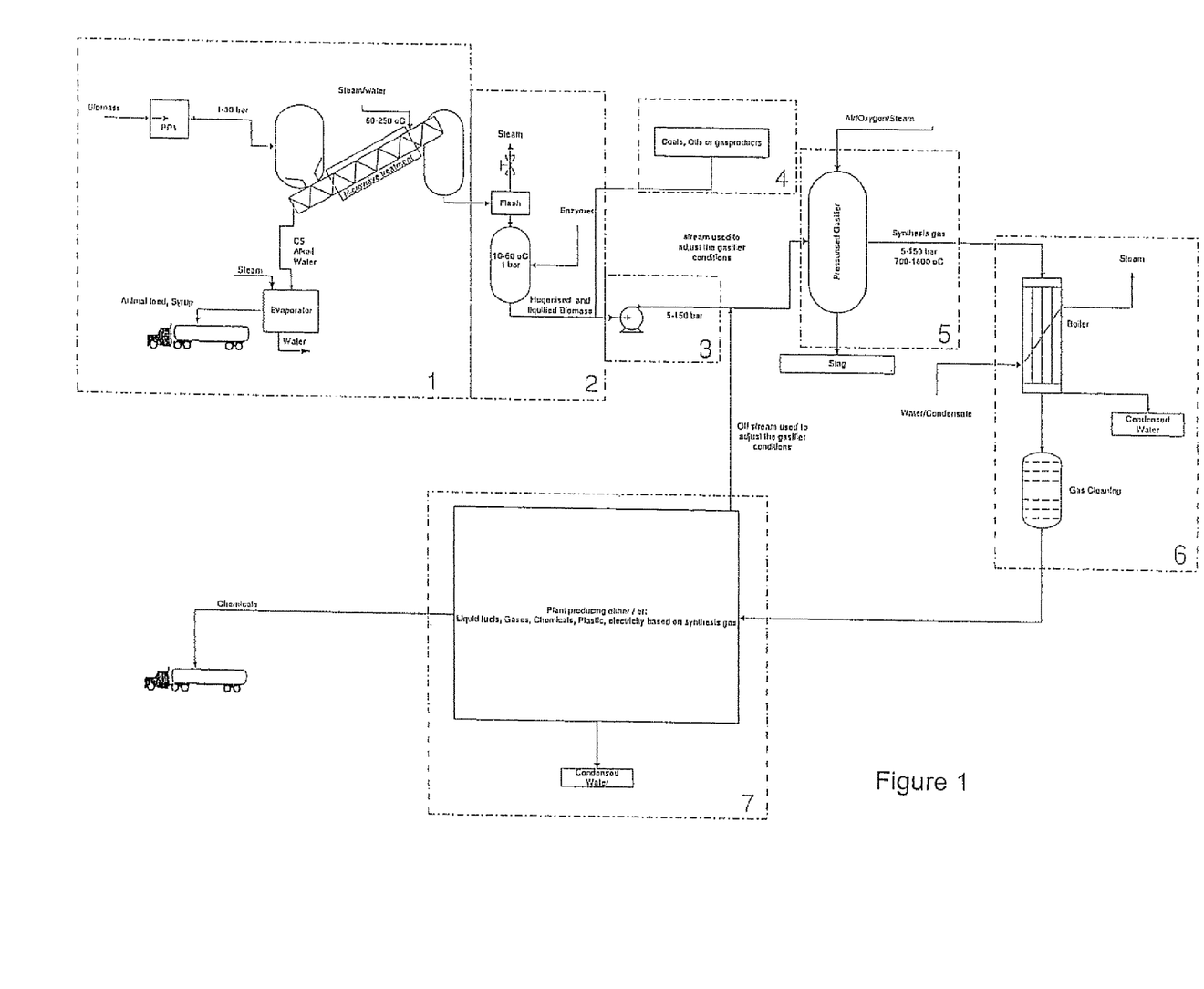
FIG. 1 shows a flowsheet from biomass to Syngas according to the present invention wherein: (1) The biomass is eventually pretreated, in order to break down eventually lignin and in order to wash out impurities as alkalies etc, (2) the biomass is liquefied by the use of enzymes to a pumpable slurry with a drymatter content above 20%, (3) the slurry is pressurised by the use of commercial available pumps, (4), the viscosity and/or calorific value is adjusted by addition of coal, oils or other hydrocarbons if necessary, (5), the slurry is gasified, preferably in a pressurised oxygen blown entrained flow gasifier, (6) the synthesis gas is cooled down and cleaned, and (7) the synthesis gas is converted into liquid fuels, other gasses, chemicals, plastic or electricity.

The processing of biomass into synthesis gas is illustrated in FIG. 1. The synthesis gas can be used to produce for instance methanol, synthetic fuel or used in Fischer-Tropsch synthesis. When synthesis gas is converted to diesel or petrol 20% of the final product consist of unusable gases. Since these gases have a high calorific value it will be beneficial to re-circulate them into the gasifier to obtain a high temperature.

DETAILED DESCRIPTION OF THE INVENTION.

As used herein, the term "biomass" refers to the biodegradable part of products, waste and remainders from agriculture (comprising compounds of both vegetable and animal origin) and forestry and from closely related industries along with the biodegradable part of waste from industry and household.

The processes of the present invention provide a degree of enzymatic hydrolysis of typically 30-50%. The liquefied biomass will consequently contain relatively large amounts of glucose, xylose, cellobiose, lignin, non-degraded cellulose and hemicellulose.

If the polysaccharide containing biomasses are lignocellulosic the pre-treatment must ensure that the structure of the lignocellulosic content is rendered more accessible to the enzymes. There are several strategies to achieve this, which all implies subjecting the lignocellulosic material to temperatures between 110-250° C. for 1-60 min e.g.:
  Hot water extraction
  Multi stage dilute acid hydrolysis
  Dilute acid hydrolyses at relatively low severity conditions
  Alkaline wet oxidation
  Steam explosion Polysaccharide containing biomasses according to the present invention includes any material containing polymeric sugars e.g. in the form of starch as well as refined starch, cellulose and hemicellulose.

Relevant types of biomasses for enzymatic hydrolysis and mixing according to the present invention may include biomasses derived from agricultural crops such as e.g.:
  Starch e.g. starch containing grains and refined starch
  DGS (residue from conventional ethanol production)
  Corn stover
  Bagasse
  Straw e.g. from rice, wheat, rye, oat, barley, rye, rape, sorghum
  Softwood e.g. *Pinus sylvestris, Pinus radiata*
  Hardwood e.g. *Salix* spp. *Eucalyptus* spp.
  Tubers e.g. beet, potato
  Cereals from e.g. rice, wheat, rye, oat, barley, rye, rape, sorghum and corn
  Waste paper, fibre fractions from biogas processing, manure, residues from oil palm processing, municipal solid waste or the like with a similar dry matter content.

If the polysaccharide containing biomasses are lignocellulosic, the material may be cut into pieces where 20% (w/w) of the biomass preferably ranges within 26-70 mm, before pre-treatment. The pre-treated material has preferably a dry matter content above 20% before entering the mixing device for liquefaction. Besides liberating the carbohydrates from the biomass, the pre-treatment process sterilises and partly dissolves the biomass and at the same time washes out potassium chloride.

The mixing performed in a liquefaction process according to the present invention serves at least a four-fold purpose.

Firstly, it ensures close contact between the enzymes used and the polysaccharide containing biomass (substrate), as this will in most cases be insoluble or only very slightly soluble.

Secondly, the mechanical work performed on the material during the mixing helps tearing larger biomass fibres and particles apart and will therefore assist in increasing the surface area of the material. This will increase the accessibility of e.g. cellulose and hemicellulose to the enzymes used. To further increase the mechanical work on the material, steel balls or similar means that will collide with the material might be added to the drum.

Thirdly, the mixing of the material prevents local accumulation of high cellobiose concentration that—as is well known for a person skilled in the art—can inhibit e.g. cellulase enzymes, especially the cellobiohydrolases.

Fourthly, an important characteristic of the cellulase enzymes is the influence of cellulose binding domains (CBD) on the enzyme performance. CBD's are functional parts of cellulose degrading enzymes. The CBD enables adhesion of the water-soluble enzyme onto an insoluble substrate surface (cellulose). The close association between the enzyme and cellulose provided by the CBD enhances the catalytic rate and stability of the enzyme. To hydrolyse cellulose, the enzyme must change the position of the CBD on the cellulose chain. It is believed that mechanical action, i.e. mixing, is important for the movement of the CBD and consequently for the enzymatic action of the enzymes along the cellulose chain.

In addition to the above it should be noted that enzymatic hydrolysis of biomass has traditionally been conducted in stirred tank reactors equipped with impellers (e.g. Rushton turbine or Intemig impeller) mounted on a centrally placed impeller shaft similar to what is used in the fermentation industry. Due to this equipment, solutions of high viscosity, very sticky or very dry material cannot be stirred efficiently but will result in zones with very poor or no mixing. Furthermore, stirrings of such solutions require very large energy inputs, which is detrimental to the process economy. Operating with polysaccharide containing biomasses this has previously restricted the upper possible limit to app. 20%. The gravity based mixing principle according to the present invention overcomes this problem and may be used for polysaccharide containing biomasses with a dry matter content up to 80%, preferably 20-50%. The principle of gravity mixing according to the present invention can easily be scaled up and be applied for all kinds of biomasses, besides refined starch, containing tip to more than 80% cellulose.

Unlike conventional stirred tank reactors traditionally used for enzymatic hydrolysis, a gravity based mixing principle, i.e. a drum mixer, a mixer with a rotary axis lifting the biomass or similar mixing devise utilising a free fall principle, at the same time enables an efficient mixing even with small power inputs and high dry matter contents and furthermore performs a mechanical processing/degradation through the forces of gravity including shear and tear forces between material and drum as well as the forces resulting from the impact between falling material and the bottom of the drum and at the same time positively effects the influence of cellulose binding domains (CBD) on enzyme performance.

Although processing of non-miscible plant materials, such as edgy polysaccharide containing biomass with relatively high dry matter content and large average fibre and particle size, is known from solid-state fermentation or bioreactors, where tumble type mixers are used for blending (Giovanozzi et all 2002), this principle has not previously been implemented in a dedicated liquefaction process for subsequent syngas production.

The present invention provides a process for liquefaction of biomasses at relatively high dry matter contents, e.g. dry matter contents between 20-80%, preferably between 20-50%. Furthermore, the process according to the present invention combines efficient liquefaction with the direct use of the end product in a gasifier.

Enzymes capable of effecting a conversion of starch, cellulose and hemicellulose or parts thereof into oligomeres and polymeres are added to the biomass either in native form or in form of microbial organisms giving rise to the accumulation of such enzymes. The pH and the temperature of the biomass are adjusted with reference to the pH-optimum and the temperature optimum of the enzymes applied.

Depending on enzyme loading, the biomass will be liquefied to a liquid without any or only with few remaining large fibres and particles within 3-24 hours. Compared to liquefaction and hydrolysis processes for subsequent fermentation of released sugars, decreased enzyme loadings can be expected.

High gravity liquefaction results in slurry with a dry-matter content of 20-50% suitable for pumping into a gasifier. Whenever the biomass is derived from household waste, a separation of unwieldy solids from the liquid phase may be particularly advantageous prior to pumping the slurry into a gasifier. At least part of the solids is removed from the biomass slurry prior to pumping of the liquid phase.

Optimally, the slurry is pumped into an entrained flow gasifier. Since a high temperature is needed in such a gasifier, hydrocarbons originating from by-products from the down stream processes might be recirculated to the gasifier. The hydrocarbons are obtained via recirculation of down-stream by-products such as off gas.

The process results in a gas having a low alkali content that can be cooled with only minor corrosion problems and thereafter cleaned from sulphur and other particles. The cleaned gas may be used as syngas for diesel, methanol, petrol or other chemicals or burned in a gas turbine for production of electricity.

The method is economically favourable and is suitable for the handling of very diverse biomasses, which makes an efficient production of syngas possible. The advantages of the present invention are that the liquified biomasses have a suitable particle size and dry-matter content for optimal feeding and gasification in a gasifier. This combination of thermal pre-treatment, enzymatic hydrolysis and gasification develop bio-fuel with a more efficient carbon utilisation than was previously possible. Furthermore, it is possible to re-deliver alkali compounds to the environment in the form of feed stuff additives.

A process according to the present invention can be performed using the following preferred technical parameters.

Dry matter content of biomass entering the gravity based liquefaction process: 20-80%, preferably 25-70%, more preferably 25-60%, even more preferably 25-50% or 25-40% and most preferably 25-35 %. Distribution of fibre and particle sizes of lignocellulosic biomass: 0-150 mm, preferably 5-125 mm, more preferably, 10-100 mm, even more preferably 15-90 mm or 20-80 mm and most preferably 26-70 mm. The preferred distribution of fibre and particle sizes is defined as at least 20% (w/w) of the lignocellulosic biomass ranging within the preferred interval.

If the polysaccharide containing biomass is lignocellulosic, it has to be pre-treated e.g. by a hot water extraction. If a hydro thermal pre-treatment is chosen the following technical set-up is preferred:

Pre-treatment temperature: 110-250° C., preferably 120-240° C., more preferably 130-230° C., more preferably 140-220° C., more preferably 150-210° C., more preferably 160-200° C., even more preferably 170-200° C. and most preferably 180-200° C.

Pre-treatment time: 1-60 min, preferably 2-55 min, more preferably 3-50 min, more preferably 4-45 min, more preferably 5-40 min, more preferably 5-35 min, more preferably 5-30 min, more preferably 5-25 min, more preferably 5-20 min and most preferably 5-15 min.

Dry matter content after pre-treatment of at least 20 w/w%, preferably 25-45%.

Enzymatic Treatment of Polysaccharide Containing Biomasses in a Gravity Mixer:

If a vessel based on the free fall mixing concept in the form of a reactor with a horizontal placed stirrer shaft lifting the biomass or similar mixing devise is used, the following technical set-up preferred:

Rotational speed, 0-30 rpm, preferably 0-20 rpm, more preferably 0-15 rpm even more preferably 0-10 rpm and most preferably 0-5 rpm.

Rotation with periodically alternated rotating direction.

Rotation in pre-defined intervals.

The optimal rotational speed will depend on the volume of the vessel, the preferred rotational speed may thus be relatively high when the process is carried out in a relatively small vessel, while it may be relatively low when the process is carried out in a relatively large vessel.

Enzymes for lignocellulosic biomass:
  Cellobiase (e.g. Novozym 188)
  Cellulase (e.g. Celluclast 1.5 FG L)
  Enzyme loading in Filter Paper Units (FPU)/g DM. 1 FPU equals the amount of enzyme necessary to hydrolyse 1 μmol/min of glycosidic bonds on Whatmann #1 filter paper, under specified conditions well known to a person skilled in the art. However, enzymatic activity could in principle be supplied in any conceivable form including through the addition of microorganisms giving rise to the desired enzymatic activity: corresponding to 0.001-15 FPU/g dry matter, preferably 0.01-10FPU/g dry matter, more preferably 0.1-8 FPU/g dry matter, more preferably 1-4 FPU/g dry matter and most preferably less than 3 FPU/g dry matter.

Enzymes for starch containing biomass:
  Enzymes in the processing of starch: alpha-amylases and glucoamylases Treatment time for enzymatic hydrolysis: 0-72 hours, preferably 1-60 hours, more preferably 2-48 hours and more preferably 3-24 hours such as 4-24 hours, such as 6-24 hours, such as 8-24 hours, such as 10-24, such as 12-24 hours, such as 18-24 hours or 22 hours. Temperature for enzymatic hydrolysis. Adjusted with reference to the optimum temperatures of the applied enzymatic activities.

pH of biomass. Adjusted with reference to the optimum pH of the applied enzymatic activities: preferably 4-12, such as 3-11, such as 5-10, such as 6-9, such as 7-8.

Addition of chemicals such as oxygen or hydrogen to increase the breakdown of lignin.

The enzymatic treatment can be conducted as a batch, fed batch or a continuous process. The obtained liquefied pumpable slurry is suitable for pumping into a pressurised gasifier such as an entrained flow gasifier. Thus, said biomass slurry primarily contains only particles below 1 mm in size, preferably below 0.9 mm, more preferably below 0.8 mm, such as below 0.7 mm, preferably below 0.6 mm, more preferably below 0.5 mm, such as below 0.4 mm, preferably below 0.3 mm, more preferably below 0.2, such as below 0.1 mm. If the calorific value of the liquefied biomass is too low in order to obtain a high outlet temperature exit the gasifier, it might be necessary to add some "extra" hydrocarbons to the gasifier. Such hydrocarbons could be recirculated by products from the petrol or diesel production, or other low value hydrocarbon products.

In general a high dry matter content of the slurry is preferred. A high dry matter content might increase the viscosity and reduce the pumpability. Adjustment of the viscosity can be made by addition of oil to the liquefied biomass, in combination with adjustment of the heating value. Another way obtain the same effect is to combine drying with a prolonged liquefaction.

EXAMPLES

Example 1

Enzymatic Liquefaction of Pre-Treated Wheat Straw

Pressed pre-treated wheat straw with an average size of approximately 40 mm (pre-treated by counter-current water extraction at 180-200° C. for 5-10 min. with water and dry matter flow ratio of 5:1) corresponding to 7 kg DW (=20 kg pre-treated straw) was put into a conventional rotary cement mixer, with a horizontal axis tilted about 10 degrees. The mixer had 2 internal ribs along the long axis to ensure mixing of the material. A lid was mounted on the opening to avoid evaporation from the mixer. The mixer drum rotated along the horizontal axis with a speed of 29 rpm.

200-1150 mL of Celluclast 1.5 FG L and 40-225 mL of Novozym 188 were added to the straw. This resulted in a final dry matter content of 30%. The enzyme loading corresponded to 3-15 FPU/g DM. The pH was adjusted to 4.8 to 5.0 by addition of sodium carbonate.

The cement mixer was heated to 40-45° C. by use of a fan heater. The mixing/hydrolysis of the material was performed for 22 hours. Depending on enzyme loading this resulted in a more or less viscous liquid without any remaining large fibres. The pre-treated straw was degraded to a paste in app. 3-5 hours. After 5-24 hours of mixing the paste was changed to a viscous liquid. Control experiments with pre-treated wheat straw only or wheat straw pre-treated at only 160° C. but using the same enzyme loading showed no sign of liquefaction of the straw.

The resulting material was centrifuged for 15 min at 2500 rpm, The supernatant was filtered through a 0.45 μm filter and analysed for sugars on HPLC. At an enzyme load of 15 FPU/g DM, the supernatant contained 70 g/L of glucose, 30 g/L of xylose after 24 hours of hydrolysis. This corresponded to 50% hydrolysis of the cellulose and hemicellulose originally present in the straw.

Example 2

Enzymatic Liquefaction and Hydrolysis at 20-40% DM

Figure 2:
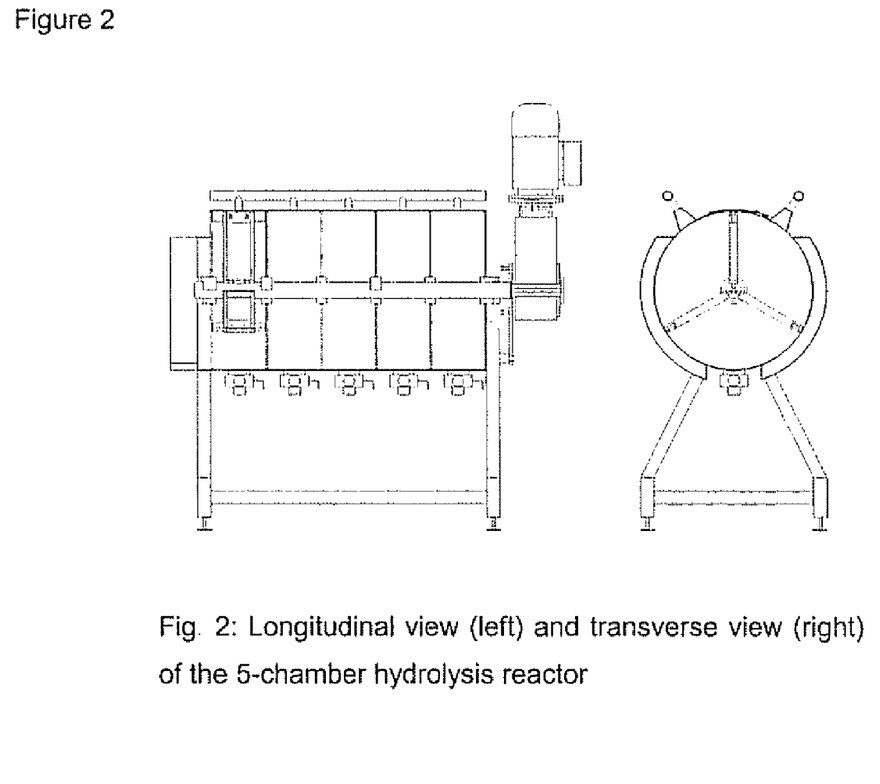
FIG. 2 shows the longitudinal and transverse view of a 5-chamber hydrolysis reactor.

The hydrolysis reactor was designed in order to perform experiments with liquefaction and hydrolysis solid concentrations above 20% DM. The reactor (FIG. 2) consisted of a horizontally placed drum divided into 5 separate chambers each 20 cm wide and 60 cm in diameter. A horizontal rotating shaft mounted with three paddlers in each chamber was used for mixing/agitation. A 1.1 kW motor was used as drive and the rotational speed was adjustable within the range of 2.5 and 16.5 rpm. The direction of rotation was programmed to shift twice a minute between clock and anti-clock wise. A water-filled heating jacket on the outside enabled the control of the temperature up to 80° C.

Figure 3:
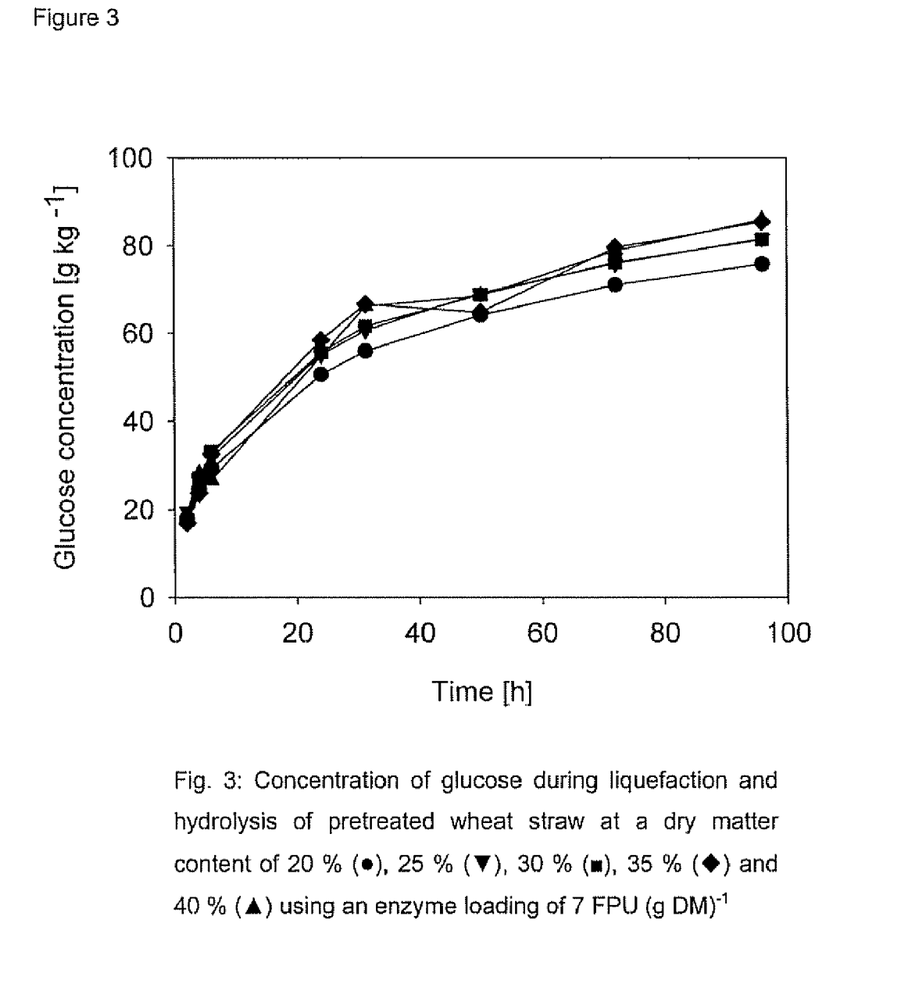
FIG. 3 shows the concentration of glucose during liquefaction and hydrolysis of pre-treated wheat straw at different dry matter contents.

The chambers were filled with pressed pre-treated wheat straw with an average size of approximately 40 mm (pre-treated by counter-current water extraction at 180-200° C. for 5-10 min. with a water and dry matter flow ratio of 5:1) and water to give an initial DM content of 20 to 40%. Celluclast 1.5 FG L and Novozym 188 in 5:1 ratio were added to give an enzyme loading of 7 FPU per g DM. The liquefaction and hydrolysis was performed at 50° C. and pH 4.8 to 5.0. The mixing speed was 6.6 rpm. Liquefaction and hydrolysis was possible with initial DM content of up to 40% DM (FIG. 3).

Example 3

Whole Crop Liquefaction (Starch and Lignocellulose)

Lignocellulosic and starch containing biomass can be processed simultaneously using gravity mixing and a mixture of cellulases, hemicellulases and amylases. The lignocellulosic biomasses may be derived from agricultural crops consisting of e.g. corn stover, straw e.g. from rice, wheat, rye, oat, barley, rye, rape and sorghum, tubers e.g. beet, potato, cereals from e.g. rice, wheat, rye, oat, barley, rye, rape, sorghum, wood consisting of softwood e.g. *Pinus sylvestris*, *Pinus radiatae* hardwood e.g. *Salix* spp., *Eucalyptus* spp., municipal solid waste, waste paper and similar biomasses.

The hydrolysis reactor described in example 3 was used for the experiments. Wheat straw (primarily a lignocellulose source) was pre-treated using counter-current water extraction at 180-200° C. for 5-10 min., with a water and dry matter flow ratio of 5:1. Wheat grain (primarily a starch source) was dry milled using a Kongskilde roller mill. The wheat grain and pre-treated straw with an average size of approximately 40 mm was mixed in a 1:1 ratio on a dry basis. DM was adjusted to between 30 and 40% DM by addition of water. Celluclast 1.5 FG L and Novozym 188 in a 5:1 ratio were added to give an enzyme loading of 7 FPU per g DM of straw. Hydrolysis of starch was done carried out using cold mash enzyme NS50033 (Novozymes A/S, Bagsvaerd, Denmark) at a loading of 3.5 g per kg of wheat grain. The liquefaction and hydrolysis was performed at 50° C. and pH 4.8 to 5.0. Mixing straw with grain resulted in a fast liquefaction and accumulation of glucose compared to just applying straw only.

Figure 4:
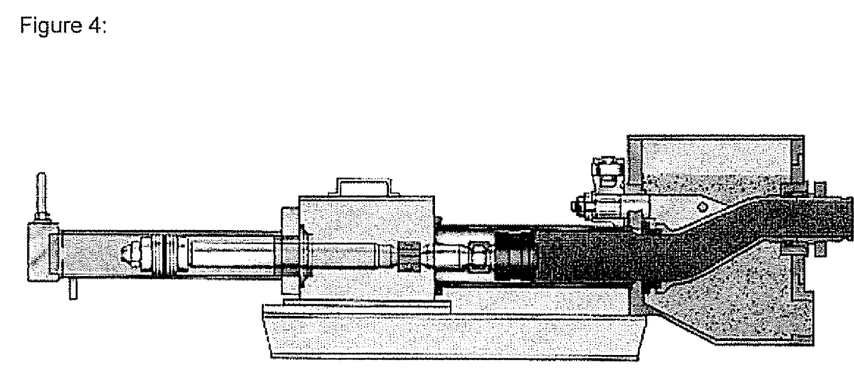
FIG. 4 shows a duplex single-acting piston pump with hydraulic actuated transfer tube without valves.

Syngas can subsequently be obtained by pumping the obtained liquefied biomass slurry into a slagging entrained flow gasifier such as a pilot scale 5 MW pressurised entrained flow gasifier. A plunger pump with special knife-edged spring-loaded cone valves can be used to develop the required pressure. A pump that has either mechanically or electrically operated suction and discharge valves to provide positive opening and closing actions will minimise plugging problems. A constant flow of slurry to a 26 bar pressurised gasifier chamber can be maintained with a screw pump. A commercial available pump is shown in FIG. 4 (http://www.directindustry.com/prod/weir-minerals-division/dry-mounted-slurry-pump-23306-56832.html). The slurry is atomised pneumatically with pressurised pure $O_2$. Optionally a pilot flame with natural gas can be kept for safety reasons and to compensate for the heat loss in the radiation screen. This will be negligible in commercial scale gasifiers.

The produced syngas is practically free of tars and $CH_4$. The syngas comprises for instance:

CO 40-50% vol; $H_2$ 25-30% vol; $CO_2$ 15-20% vol; $N_2$ 7-11% vol; $CH_4$ less than 0.1% vol; $H_2S$ 15-30 ppm Especially the $N_2$ and $H_2S$ content will be very dependent on the type of biomass used.

In a commercial slagging entrained flow gasifier, a pressure of 40 bar and 1300-1500° C. will be sufficient. Slag and ash is recycled. If the calorific value of the liquefied biomass is too low in order to obtain a high outlet temperature exit the gasifier, it might be necessary to add some "extra" hydrocarbons to the gasifier. Such hydrocarbons could be recirculated by products from the petrol or diesel production, or other low value hydrocarbon products.

In general a high dry matter content of the slurry is preferred. A high dry matter content might increase the viscosity and reduce the pumpability. Adjustment of the viscosity can be made by addition of oil to the liquefied biomass, combined with adjustment of the heating value. Another way to obtain the same effect is to combine drying with a prolonged liquefaction.

CITED REFERENCES

DE10210178. Treating flowable materials in super-critical water comprises producing aqueous educt stream from flowable materials and heating, heating water stream to super-critical temperature and mixing both streams in reactor. Forschungszentrum Karlsruhe GmbH.

ECN: van der Drift, A, Boerrigter H., Coda B., Cieplik M. K., Hemmes K. Entrained flow gasification of biomass. Ash behaviour, feeding issues, and system analysis, ECN-report C-04-039, 2004.

Giovannozzi-Sermanni, G., D'Annibale, A., Perani, C., Porri, A., Falesiedi, G. (2002). Solid-state bioreactors for the sustainability. http://www.unitus.it/dipartimenti/dabac/progetti/ssbioreactors/solidstatebioreactor.htm Hamelinck C N, Faaij A P C, Uil H, Boerrigter H. Production of FT fuels from biomass, March 2003, ISBN 90-393-3342-4

Henrich E., Dinjus E. Tar-free, high pressure synthesis gas from biomass. Expert Meeting on Pyrolysis and Gasification of Biomass; Strassbourg, France; 30 Sep.-1 Oct. 2002.

LLC: Frontline BioEnergy, LLC. What is biomass? http://www.frontlinebioengergy.com/id15.html (16 May 2006)

RRI: Research Reports International. Gasification for Power Generation. 1st Edition—September 2005

The invention claimed is:

1. A method for syngas-production from polysaccharide containing biomass comprising the steps of:
    subjecting a polysaccharide containing biomass having a dry matter content above 20% to enzymatic liquefaction and hydrolysis into oligomeres or polymeres to thereby yield a biomass slurry having a dry matter content between 20 and 50%;
    transferring said biomass slurry by pumping said biomass slurry into a pressurised gasifier; and
    gasifying said biomass slurry to thereby produce syngas.

2. A method for syngas-production from polysaccharide containing biomass comprising the steps of:
    liquefying a polysaccharide containing biomass having a dry matter content above 20% by enzymatic hydrolysis and mixing using a free fall type mixing that provides mechanical degradation of the biomass during hydrolysis to thereby yield a biomass slurry having a dry matter content between 20 and 50%;
    transferring said biomass slurry by pumping into a pressurised gasifier; and
    gasifying said biomass slurry to thereby produce syngas.

3. A method according to claim 1, wherein at least part of the solid phase has been removed from said biomass slurry prior to pumping of the liquid phase.

4. A method according to claim 1, wherein said liquid biomass slurry resulting from said enzymatic hydrolysis contains primarily particles less than 1 mm in size.

5. A method according to claim 1 wherein the viscosity of said biomass slurry is modified prior to it being pumped into said pressurised gasifier.

6. A method according to claim 5, wherein said modification of viscosity is obtained by drying or by the addition of oils.

7. A method according to claim 1, wherein hydrocarbons are added together with the biomass to the pressurised gasifier.

8. A method according to claim 7, wherein said hydrocarbons are obtained via recirculation of down-stream by-products.

9. A method according to claim 1 wherein a slagging additive is added to said biomass slurry prior to its transfer into said pressurised gasifier.

10. A method according to claim 1 wherein alkali-salts are removed from said biomass prior to said biomass slurry being transferred into said pressurised gasifier.

11. A method according to claim 10 wherein said alkali-salts are removed and collected together with sugars in a form suitable for nutritive additive to feeding stuff.

12. A method according to claim 1 wherein said polysaccharide containing biomass slurry having a dry matter content of above 20% is derived from the biodegradable part of products, waste and remainders from agriculture comprising compounds of both vegetable and animal origin, or forestry and closely related industries, or from the biodegradable part of waste from industry and household.

13. A method according to claim 1 wherein said polysaccharide containing biomass slurry having a dry matter content of above 20% is a lignocellulosic biomass or part thereof derived from agricultural crops, municipal solid waste, waste paper, fibre fraction from processing of biogas, or manure.

14. A method according to claim 1 wherein said polysaccharide containing biomass slurry having a dry matter content of above 20% is starch.

15. A method according to claim 1 wherein polysaccharide containing biomass slurry having a dry matter content of above 20% is a mixture of starch and lignocellulosic biomasses derived from agricultural crops, municipal solid waste, or waste paper.

16. A method according to claim 15 wherein said polysaccharide containing biomass slurry having a dry matter content of above 20% has been subjected to a thermal pre-treatment.

17. A method according to claim 16 wherein said thermal pre-treatment includes the addition of chemicals inducing lignin degradation.

18. A method according to claim 1 wherein the dry matter content of the polysaccharide containing biomass after pretreatment and liquefaction is between 25-80%.

19. A method according to claim 1 which is carried out as a batch, a fed-batch, or a continuous process.

20. A method according to claim 1 wherein the polysaccharide containing biomass comprises primarily pre-treated lignocellulosic biomass.

21. A method according to claim 20 wherein the distribution of particle sizes and fibers of said biomass before pre-treatment is such that at least 20% fall within the range of 26-70 mm.

22. A method according to claim 8, wherein the downstream by-product is off gas.

23. A method according to claim 13, wherein the agricultural crops are selected from the group consisting of corn stover, bagasse, straw, tubers, cereals, softwood, and hardwood.

24. A method according to claim 23, wherein:
the straw is selected from the group consisting of rice, wheat, rye, oat, barley, rape, and sorghum;
the tubers are selected from the group consisting of beet and potato;
the cereals are selected from the group consisting of rice, wheat, rye, oat, barley, rape, and sorghum;
the softwood is selected the group consisting of *Pinus sylvestris* and *Pinus radiata*; and
the hardwood is selected the group consisting of *Salix* spp. and *Eucalyptus* spp.

25. A method of claim 14, wherein the starch comprises starch containing grains or refined starch.

26. A method according to claim 15, wherein the agricultural crops are selected from the group consisting of corn stover, straw, tubers, cereals, softwood, and hardwood.

27. A method according to claim 26, wherein:
the straw is selected from the group consisting of rice, wheat, rye, oat, barley, rape, and sorghum;
the tubers are selected from the group consisting of beet and potato;
the cereals are selected from the group consisting of rice, wheat, rye, oat, barley, rape, and sorghum;
the softwood is selected the group consisting of *Pinus sylvestris* and *Pinus radiata*; and
the hardwood is selected the group consisting of *Salix* spp. and *Eucalyptus* spp.

* * * * *